United States Patent [19]

Pecen

[11] Patent Number: 4,641,967
[45] Date of Patent: Feb. 10, 1987

[54] PARTICLE POSITION CORRELATOR AND CORRELATION METHOD FOR A SURFACE SCANNER

[75] Inventor: Jiri Pecen, Palo Alto, Calif.

[73] Assignee: Tencor Instruments, Mountain View, Calif.

[21] Appl. No.: 786,620

[22] Filed: Oct. 11, 1985

[51] Int. Cl.⁴ .................................. G01N 21/00
[52] U.S. Cl. .......................... 356/237; 364/491
[58] Field of Search .................. 356/237, 398; 250/492.2, 562, 563, 572; 358/106; 364/491

[56] References Cited

U.S. PATENT DOCUMENTS 4,559,603 12/1985 Yoshikawa .................. 356/237 X

OTHER PUBLICATIONS

Untitled article by A. Neukermans, dated Jan. 13, 1986.

Primary Examiner—Eugene R. LaRoche
Assistant Examiner—Robert J. Pascal
Attorney, Agent, or Firm—Thomas Schneck

[57] ABSTRACT

A method and apparatus for particle detection and position correlation that fuses separate detections of the same particle on adjacent scan lines into one. A first scan line on a surface is scanned with a laser beam and the scattered light detected. The detection generates address and amplitude data for each particle which is stored. The second line scanned also generates data which is stored in a buffer. Particle data between scan lines is compared. Data for new particles is stored, data for previous particles no longer detected being sent to computer storage, and data for the same particle being compared and only the one with larger amplitude being kept. The results in computer storage may be displayed as a wafer with those pixels lit which have particles.

13 Claims, 7 Drawing Figures

PARTICLE POSITION CORRELATOR AND CORRELATION METHOD FOR A SURFACE SCANNER

TECHNICAL FIELD

The present invention relates to optical flaw and contaminant detect and in particular to apparatus and processes for accurately particle positions and count on a scanned surface.

BACKGROUND ART

U.S. Pat. No. 4,378,159 to Galbraith, assigned to the assignee of the present invention, discloses a scanning laser contaminant and defect detector for reflective surfaces having a laser capable of generating a laser beam, a support holding the surface to be inspected, mirrors and other optics for directing and sweeping the beam in a path across the test surface, a light collector, and a light detector for detecting light scattered from the test surface.

In U.S. Pat. No. 4,402,605 to McVay et al., oscillation of a scanning mirror and advance of a plate provides a timing reference to locate particles on the plate. The detector may include a comparator with an adjustable threshold level for generating a signal only when the received scattered radiation exceeds the threshold. The amount of scattering is generally proportional to the size of the particle.

In U.S. Pat. No. 4,482,902 to Bailey et al. a reference clock is used in a scanning system to address memory where pixels identifying the position of particles are recorded. The successive addresses contain pixel location defining codes that compensate for the nonlinearity of a sinusoidal scan rate.

The semiconductor industry uses contaminant detectors to determine the number, size and position of particles on a wafer containing integrated circuits. In this industry, particle detection is particularly important for integrated circuits made using very-large-scale-integration (VLSI) technology. A small number of contaminants can disable a VLSI circuit, so an exact count is necessary to accept or reject wafers and in general provide good quality control.

Unfortunately, laser scanning detectors of the prior art generally overcount the number of particles, because laser beams have a Gaussian intensity distribution and a finite width. While scanning for particles along one path, the "tail" of the beam may cause scattering from particles in adjacent paths. A particle may thus be counted more than once leading to the undesired overcounting. Noise from stray light may also be detected and counted as a particle. Further, when displaying the position of particles with pixels, a pixel is lit when a particle is detected by a beam in that pixel location. Particles near a pixel border may thus light more than one pixel giving inaccurate position information.

An object of the present invention is to devise a method and apparatus for accurately counting the number and determining the position of particles detected by a surface scanner.

Another object of the invention is to devise a method to accurately display the location of particles on the surface, where one particle does not light up more than one pixel.

DISCLOSURE OF THE INVENTION

The above objects have been met with a particle position correlator and position correlation and display process for a surface scanner in which multiple particle detections are "fused" into one before storage in computer memory, counting and display. The particle position correlator has an input buffer connected to a scattered light detector for receiving scattering amplitude data and receiving an address. The address includes a scan line number and a Y-address. The input buffer stores the address and amplitude data for the entire current line. A memory connected to the input buffer stores address and amplitude data kept from previous scan lines. An address comparator and a data comparator compare Y-address and amplitude data respectively between the current and previous scan lines. Each comparitor connects to the input buffer for receiving address and data from the current scan line and to the memory for receiving address and data stored from previous scan lines. A FIFO stack connects to the comparators and to an output buffer for sending finished address and amplitude data of fused particle information to computer storage.

The process comprises steps for receiving address and amplitude data relating to a current scan line, storing this information in the input buffers, comparing address and data relating to the current scan line with address and data from previous scan lines stored in memory, and storing the results of the comparison in memory, and sending finished address and amplitude data to computer storage. When comparing current and previous scan line files, first the addresses are compared. If a Y-address relating to the previous scan line does not match any Y-address relating to the previous scan line, then a particle previously detected is no longer seen and the address and amplitude data is sent via the FIFO stack and output buffer to computer storage. If a Y-address relating to current and previous scan lines match, then this is the same particle, and the address and amplitude data for the scan line with a larger amplitude value is stored in memory, while the smaller data are discarded. In this manner, multiple particle detections from a single particle are fused, and an accurate particle count can be obtained. Other features and advantages will be seen in the discussion below.

BEST MODE FOR CARRYING OUT THE INVENTION

Figure 1:
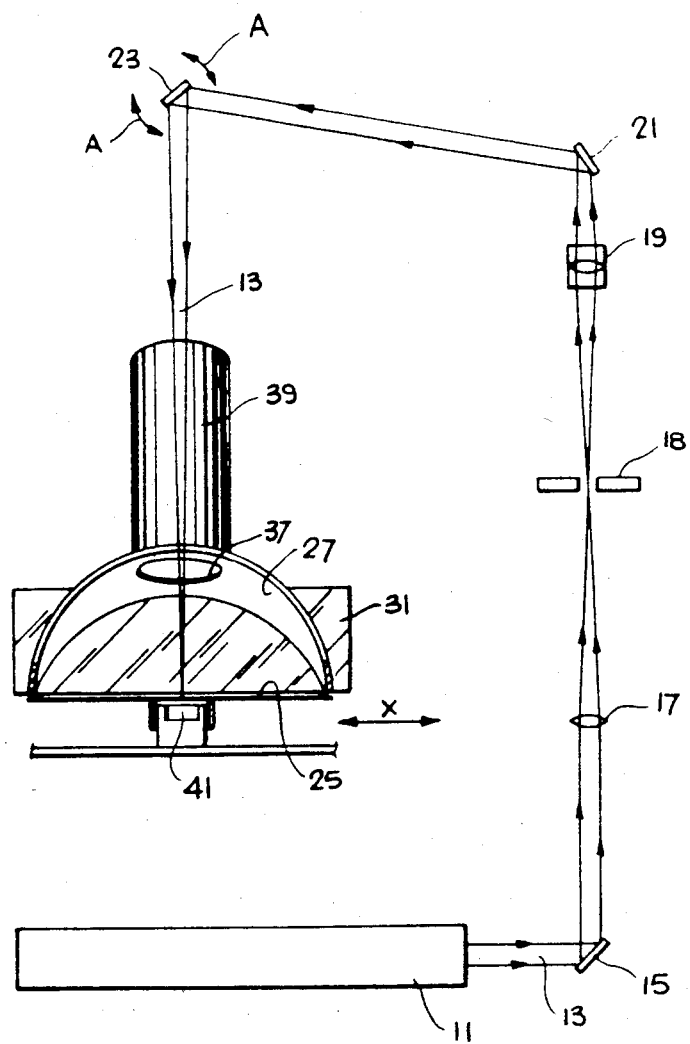
FIG. 1 is a simplified plan view of the optical contaminant detector used in the present invention.

With reference to FIG. 1, a low power laser 11 may be seen directing a beam 13 toward mirror 15. Laser 11 can be a helium-neon general purpose laser having an output power of a few milliwatts. A higher power laser may be preferable for greater detection capability. In some instances blue light, e.g. from a helium-cadmium laser is preferred for detection of smaller defects than with a helium-neon laser. Beam 13 is directed to focussing lens 17 and then to a beam collimating and focussing lens 19. A spatial filter 18 a short distance from lens 17 allows only the central portion of the beam to proceed. The focal length of lens 19 is approximately 14 cm. From lens 19, the beam is directed toward fixed mirror 21 and then to galvanometer mirror 23. Galvonometer mirror 23 directs light so that the focal point of the beam is at the surface of the surface 25. The focal length of focussing optics 19 is long enough so that the beam stays in focus as it is swept across the surface 25, even though the beam makes a slightly arc-shaped trajectory. There is sufficient depth of field at this long focal length that a fine beam spot is maintained as the beam sweeps across the surface being scanned for defects. Because of this long focal length, the beam generally remains perpendicular to the surface 25 being scanned.

The defect need not be highly reflective. Reflectivity above 7 to 10% is sufficient to be detected with a low power, helium neon laser with a sensitive detector, such as a photomultiplier tube, and the light collector of the present invention.

The light collector 27 is a sector, preferably a quadrant, of a spherical shell. The shell has a reflective coating, such as white paint, on the inside surface, facing surface 25, and an absorptive coating, such as black paint, on the outside surface. For purposes of illustration, only one-half of the shell is shown in FIG. 1. That half is shown resting on mirror surface 31 which forms half of a V-shaped trough in which the shell 27 rests. Shell 27 has a slit through which beam 13 enters. This slit is not visible in FIG. 1. The beam passes through an exit aperture 35, visible in Fig. 2, which is opposite the beam entrance aperture.

The upper portion of the shell is termed a "crown". The inner crown surface directs light toward the mirrors, then back to the crown, and so on, until light enters the detector. Note that the shell is positioned in proximity to the surface 25 with the crown distal to the test surface and the bottom of the V-shaped trough formed by the mirror side walls in close proximity to the test surface. This is done in order that a gap between the V-shaped walls, which forms the beam exit port, be very close to the test surface. Moreover, close proximity, within a few millimeters, allows most of the scattered light from the test surface to reenter the light collector. Specularly reflected light doubles back on the beam path toward the galvanometer mirror and is lost. On the other hand, light scattered at an angle to the incident beam is collected for measurement by the detector.

The V-shaped mirror side walls have two distinct functions. First, the walls serve to optically fold the sector, allowing for a compact collector. Second, the linear gap between the base of the side walls serves as a beam exit port for a scanning beam along a linear scanning path. Each of the side walls is inclined to the vertical by an angle of 45 degrees.

A detector port 37 is defined in the shell at an acute angle with the beam entrance port relative to test surface 25. A light detector, such as a silicon cell or preferably a photomultiplier tube 39 is mounted directly over the director detector port, in a light-tight relationship therewith.

The galvanometer mirror 23 moves back and forth at a high rate, such as 400 sweeps per second, in directions indicated by the arrows A. This causes the beam to move back and forth across test surface 25 in the Y direction. Independently of this motion, surface 25 is advanced in the X direction by a transport 41 on which the test surface is carried. Sensors at each end of test surface detect the beginning and end of a scan line and reset a clock. The clock typically operates at 16 MH and provides a Y-address for the scan beam within one clock cycle (62.5 nsec).

Figure 2:
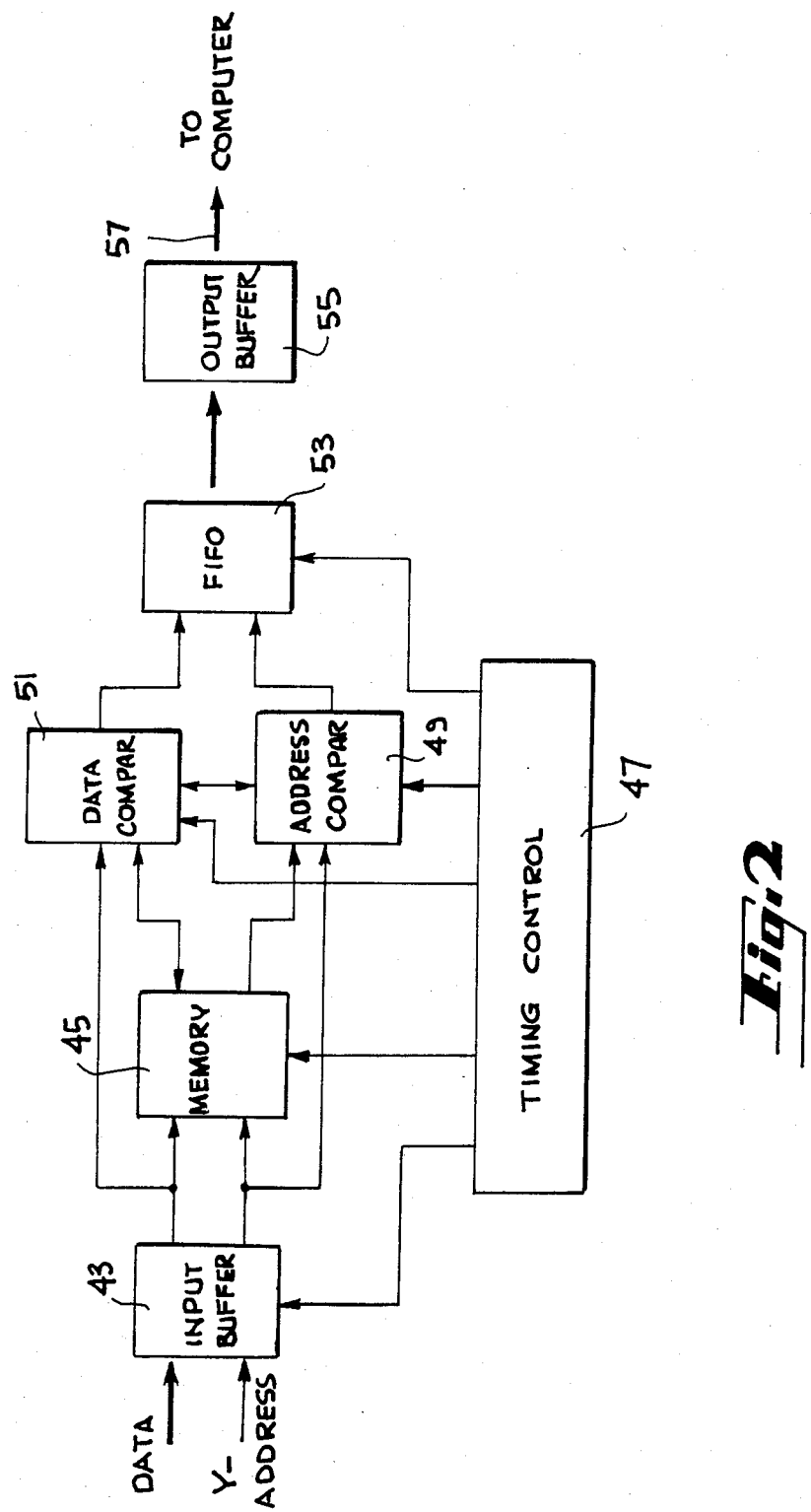
FIG. 2 is a block diagram of the particle position correlator of the present invention.

In FIG. 2, particle data coming from a single scan line are stored sequentially in an input buffer 43. Typically, buffer 43 may have as many as 1024 storage locations. Particle data from previous scans are stored in a second buffer or memory 45 with an equal number of storage locations. Particle data includes a scattering amplitude value and a corresponding address made up of a scan line number and a Y-address. As a particle is scanned by the beam, the peak amplitude of the scattered beam, or alternatively the integrated amplitude, is digitized and sent to input buffer 43 as a scattering amplitude value, hereafter referred to as amplitude data.

Both the input buffer 43 and memory 45 are thus typically three bytes wide. One byte contains amplitude data while the other two bytes contain the address. Memory 45 is a combination of all the previous scan lines as will be explained below. Buffer 43 and memory 45 may be thought of as sequential files which represent particle detections and which are read in a top-down fashion.

Under the control of a timing control 47 an address comparator 49 receives a Y-address from both buffer 43 and memory 45. Comparator 49 compares a Y-address from buffer 43, representing the current scan line with a Y-address from memory 45, representing previous scan lines. Two Y-addresses are said "match", representing the same particle, when they are the same or different within a preset number of clock cycles from each other. Typically, the Y-addresses match when they are not more than one or two cycles apart.

If Y-addresses match, that is the current particle data has a corresponding previous particle datum, the amplitude data is compared in a data comparator 51. Data comparator 51 is corrected to receive the amplitude data from input buffer 43 and memory 45. The particle detection having a larger amplitude value is stored with its address in memory 45, while the other amplitude data is discarded. If the amplitudes are equal, no exchange takes place. In this way, all detections of a particle are reduced or "fused" into one.

If a Y-address stored in the current scan line file in input buffer 43, lacks a matching Y-address in the previous scan files in memory 45, then a new particle has been detected. An amplitude comparison is again made by data comparator 51. Here the comparison simply results in a transfer of current data in input buffer 43 to memory 45. The net result is a new entry in memory 45 having both an amplitude and its corresponding address of the new particle.

If a Y-address stored in a previous scan line file in memory 45 lacks a matching Y-address in the current scan files in buffer 43, then a particle which previously had been detected is no longer seen by the beam. An amplitude comparison is again made by data comparator 51. Since there is no corresponding amplitude data in buffer 43, the comparison results in a transfer of the previous data to a FIFO stack 53. This entry is removed from memory 45. FIFO stack is connected to comparitors 49 and 51 and receives particle data only when all detections for a particle have been considered. An output buffer 55 connects to FIFO stack 53 and sends data in FIFO 53 to computer storage via an external bus 57. The particle data in computer storage is ready for display, counting, or further processing by computer.

In addition to the three-byte wide memory 45 discussed above, a four-byte wide memory may also be used, including a byte for counting the number of particle detections for each particle. Wherever a new particle is detected and stored in memory, the particle detection count is set to one. After each additional detection, the address and amplitude are compared as before. Each time the address comparator determines that the same particle is detected, the particle detection count is incremented by one. When a particle is no longer detected, the comparitor sends the particle data to the FIFO stack for computer storage only if the particle count is in a preset range. Typically, this range has a lower limit of one. If a detection occurs only once the detection might be assumed to be noise and the data might be discarded. Typically, this range also has an upper limit. If the detection occurs more than the upper limit, the detection is assumed to be that of a line on the surface rather than a particle. Lower and upper limits to the range are variable.

Figure 3:
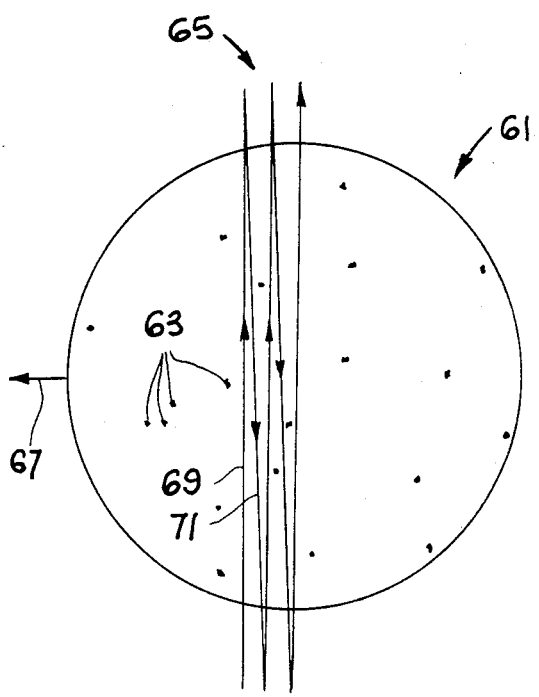
FIG. 3 is a top plan view of a wafer with particles being scanned by the detector in FIG. 1.

In FIG. 3, a semiconductor wafer or other surface 61 to be scanned contains particles 63 thereon. Particles 63 vary in size but are typically about one micrometer in diameter. A laser beam scans surface 61 in a back-and-forth series of sweeps 65. Each sweep takes about 2.5 milliseconds, there being about 400 sweep cycles per second. At the same time, surface 61 is transported in a direction orthogonal to the sweeps 65, as indicated by arrow 67. As a result, each sweep 65 is spatially separated on surface 61 from the preceding sweep thereby forming adjacent scan lines, such as lines 69 and 71. Each scan line is typically separated by about 25 micrometers.

Figure 4:
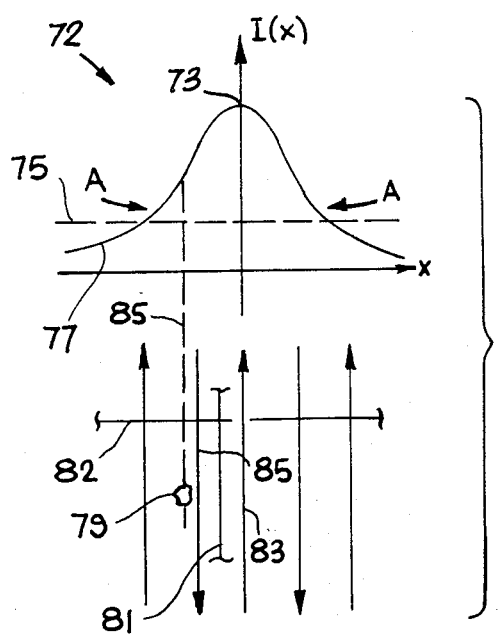
FIG. 4 is a graph of a Gaussian beam intensity distribution in conjunction with an enlarged plan view of the scanning of the wafer in FIG. 2.

In FIG. 4, a scanning laser beam 72 typically has a Gaussian intensity distribution $$I(x) = I_o \exp\{-(w/\sqrt{2x})^2\}$$

where $I_o$ is a peak intensity at the center of the beam 73 and W is the full width measured at $1/e^2$ of the peak intensity. Typically, the scanning beam has a full width, as represented in FIG. 4 by arrows A—A, of about 100 micrometers. Thus the beam 72 has a width substantially larger, usually four to six times larger, than the scan line separation.

Light scattered from the surface 61 in FIG. 3 is detected when the intensity is above a threshold value. The threshold depends on both the light gathering power of the surface scanning system and the sensitivity of the detector. In addition, the threshold may be adjusted by using a comparator that generates an amplitude value signal only when the received amplitude is above a preset value. The threshold is typically adjusted to detect particles at lower scattering amplitudes and so that separate particles are not fused into one. In any case, the intensity of the beam striking a particle must be above a threshold value, indicated by dashed line 75 in FIG. 4, to detect the particle. A portion 77 of Gaussian beam 72 is below threshold.

A particle 79 is seen lying near a pixel boundary 81. Pixel boundaries 81 and 82 are not physical features on the surface being scanned and are shown in FIG. 4 only for illustration. The current scan line 83 is to the right of pixel boundary 81. Beam 72 strikes particle 79 with an intensity above threshold 75, as seen by dashed line 85. Thus particle 79 is detected even though it does not lie in the pixel currently being scanned. Particle 79 is also detected with a larger amplitude value by scanning a scan line 85. In the prior art, both pixels to the left and right of pixel boundary 81 would be lit, indicating detection. In the present invention, however, the detection by scanning on scan line 83 is discarded in favor of the larger amplitude value detected on scan line 85. Thus only the pixel to the left of pixel boundary 81 is lit. Further, the separate detections are fused by the position correlator described with reference to FIG. 2 into one detection yielding an accurate particle count.

Figure 5:
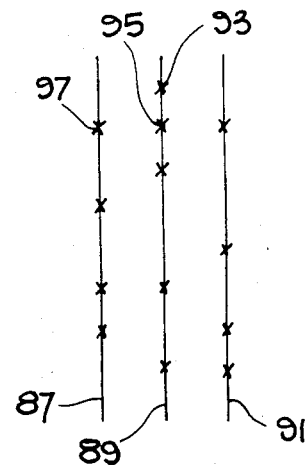
FIG. 5 is a schematic illustration of the process of the present invention.

With reference to FIG. 5, a schematic representation of detections on three scan lines 87, 89 and 91 illustrates the process of the present invention. Each X represents a particle detection. Detections on the same horizontal row represent detections in which Y-addresses match. When scan line 89 is scanned, particle detection data is received and stored in a buffer. Data from scan line 87 and prior scan lines are stored in a second buffer or memory.

Detection 93 represents a new particle since no corresponding detection in scan line 87 has a matching Y-address. Particle data relating to detection 93 is stored in memory. Detection 95 represents another detection of a previously detected particle. Detection 97 on scan line 89 has a matching Y-address with detection 95. The amplitude data for detection 95 and the stored amplitude for scan line 87 or earlier are compared. Particle data for the detection data with the large amplitude data is stored in memory. Particle data for the other detection is discarded. In scan line 91, no particle detection has a matching Y-address with detection 93. Data for detection 93 is sent to a FIFO stack for delivery to computer storage.

There are thus three major operations to be done depending on whether, in a scan line, a new particle is detected, the same particle is detected or a previously detected particle is no longer detected. Data for new particles are stored in memory. Data for the same particle is compared with previous data stored for that particle, and the data with the larger amplitude value is stored. Data for particles no longer detected are sent to computer storage.

Figure 6:
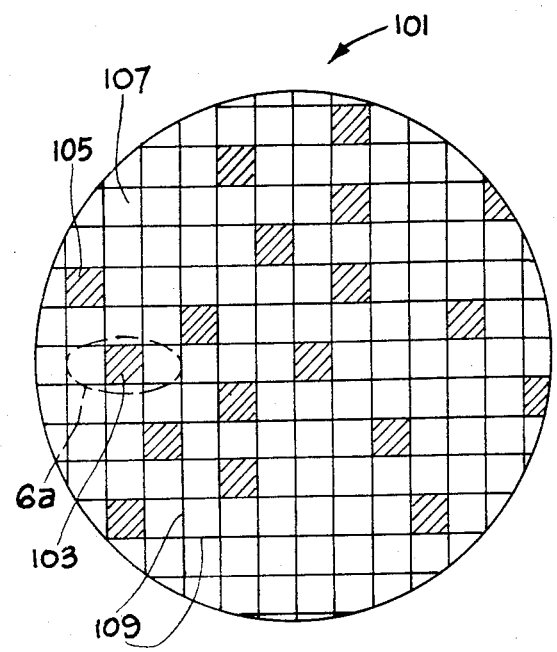
FIG. 6 is a plan view of a display of particles on the wafer in FIG. 3 in accord with the present invention.

In FIG. 6, particle detection data in computer storage is displayed as pixels 103, 105, and 107 on a wafer 101. Each pixel has a dimension substantially larger than the separation between scan lines, such as scan lines 96 and 71 in FIG. 3. Typically, each pixel is a square 10 to 16 scan lines wide. There are potentially a large number of particles for a pixel. A pixel 103, for example, has 3 particles. A pixel 105 is lit when at least one particle lies on the wafer in that pixel. Pixels, such as pixel 107, having no particle detections remain unlit.

Figure 6A:
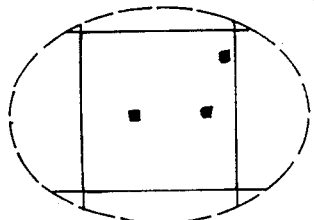
FIG. 6a is an enlarged pixel in FIG. 3 in accord with an alternate embodiment of the present invention.

In an alternate embodiment shown in FIG. 6a, a pixel in FIG. 6 is displayed in an enlarged format. Enlarged pixel shows each particle detected in a pixel. Each particle displayed in the enlarged pixel corresponds to an address derived with the correlation process of the present invention. As a result, even particles spaced together closer than the beam width can be distinguished and displayed.

I claim:
.claims

1. A process of particle detection and position correlation comprising,
   (a) scanning a first scan line on a surface with a laser beam having a characteristic beam width, scattering of said laser beam from said surface being detected when a scattering amplitude is above a threshold value, a Y-address of said scanning beam being generated during said scanning,
   (b) storing data from said scanning of said first line, as previous data, said data identifying an address having a scan line number and a Y-address, said data also including scattering amplitude data at each said address,
   (c) scanning a second line with said laser beam, said second scan line being spaced a distance less than the beam width from said first scan line, scattering of said beam again being detected, data from said scanning of said second line being stored as current data,
   (d) comparing said current data with said previous data, current data that lack a corresponding previous datum with a matching Y-address being stored as previous data, said current data having a corresponding previous datum with a matching Y-address replacing said previous datum when said amplitude data of said current data has a value larger than that of said previous datum,
   (e) sending previous data that lack a corresponding current datum with a matching Y-address to a computer storage, and
   (f) repeating steps (c)-(e) for third, fourth and succeeding scan lines until the entire surface is scanned.

2. The process of claim 1 further comprising counting between step (d) and step (e) the number of scan lines with a particular Y-address corresponding to a particular particle detection, said previous data being sent in step (f) only when said number of scan lines counted is in a preset range, said previous data lacking a corresponding current datum with a matching Y-address being discarded when said number of scan lines counted is outside said preset range.

3. The process of claim 2 wherein said preset range has a lower limit of two corresponding to noise and an upper limit of twelve corresponding to a surface line.

4. The process of claim 1 further comprising displaying said data in computer storage or a grid of pixels, said pixels having a characteristic dimension substantially larger than said separation between succeeding scan lines, a pixel being lit when at least one address corresponding to a pixel is in computer storage.

5. The process of claim 4 further comprising enlarging at least one of said lit pixels, said pixel having a plurality of subelements, each subelement corresponding to an address, a subelement being lit when said corresponding address is in computer storage.

6. A particle position correlator for use in a surface scanner comprising,
   means for receiving addresses and corresponding scattering amplitude data relating to particle detection on a current scan line,
   means for storing said addresses and data, some of said addresses matching addresses stored from previous scan lines, the rest of such addresses corresponding to new particle detections,
   means for comparing said addresses and said amplitude data relating to said current scan line with said addresses and corresponding amplitude data stored from said previous scan lines, said amplitude data being compared when said compared addresses match, one of said compared amplitude data having a larger amplitude value being stored in said storing means with the address to which said one corresponds, the other of said compared amplitude data and the address to which the other corresponds being discarded, and
   means for sending said addresses and data stored from previous scan lines that lack a matching address relating to said current scan line to an output for computer storage, said sent addresses and data corresponding to finished particle detections.

7. The particle position correlator of claim 6 wherein said receiving means comprises an input buffer receiving amplitude data relating to a current scan line from a light detector in a surface scanner, said input buffer connected to said storing means storing said addresses and data and to said comparing means.

8. The particle position correlator of claim 6 wherein said sending means comprises a FIFO stack connected on an input end to said comparing means, and an output buffer connected to an output end of said FIFO stack to receive addresses and data to be sent and connected via an external bus to a computer storage.

9. The particle position correlator of claim 6 further comprising a means for counting the number of scan lines with a particular address corresponding to a particle detection, said addresses and data stored from previous scan lines that lack a matching address relating to a current scan line being discarded when the number of scan lines counted for said addresses is outside a preset range.

10. The particle position correlator of claim 9 wherein said preset range has a lower limit of two corresponding to noise and an upper limit of twelve corresponding to a detected surface line.

11. The particle position correlator of claim 6 wherein said addresses comprise a scan line number and a sweep clock count.

12. A particle position correlator for use in a surface scanner comprising,
   an input buffer receiving scattering amplitude data relating to particle detection on a current scan line from a light detector in a surface scanner and receiving addresses corresponding to said data, each of said addresses including at least a scan line number and a Y-address,
   means connected to said input buffer for storing said addresses and data, some of said addresses matching addresses stored in said storing means from previous scan lines, the rest of said addresses corresponding to new particle detections,
   means connected to said input buffer and to said storing means for comparing said addresses and said corresponding amplitude data relating to said current scan line with said addresses and corresponding amplitude data stored in said storing means from said previous scan lines, said corresponding amplitude data being compared when said compared addresses have matching Y-addresses, one of said compared amplitude data having a larger amplitude value being stored in said storing means with the address to which said one corresponds, the other of said compared amplitude data and the address to which said other corresponds being discarded, means for counting the number of scan lines with a particular Y-address corresponding to each particle detection, a FIFO stack connected at an input end to said comparing means, and an output buffer connected to an output end of said FIFO stack and connected via an external bus to a computer storage, said addresses and data stored from previous scan lines that lack a matching Y address relating to a current scan line being sent to said computer storage via said FIFO stack and said output buffer when the number of scan lines counted for said particular Y-address is in a preset range, and being discarded when the number of scan lines counted for said particular Y-address is outset said preset range.

13. The particle position correlator of claim 12 wherein said preset range has a lower limit of two corresponding to noise and an upper limit of twelve corresponding to a detected surface line.

* * * * *